United States Patent [19]

Winn

[11] 4,081,449
[45] Mar. 28, 1978

[54] HETEROCYCLIC ESTERS OF ALKYLPHENYL BENZOPYRANOPYRIDINES

[75] Inventor: Martin Winn, Waukegan, Ill.

[73] Assignee: Abbott Laboratories, North Chicago, Ill.

[21] Appl. No.: 348,367

[22] Filed: Apr. 5, 1973

[51] Int. Cl.$^2$ .................................. C07D 491/04
[52] U.S. Cl. ..................... 260/293.58; 260/256.4 H; 260/268 TR; 260/294.8 B; 260/295 T; 260/297 T; 260/590 D; 260/613 R; 260/613 A; 260/619 R; 424/246; 424/248.55; 424/250; 424/251; 424/256; 424/267; 544/55; 544/60; 544/126; 544/96
[58] Field of Search ............ 260/243 B, 247.5 R, 260/268 TR, 293.58, 326.5 CA, 295 T, 294.8 B, 256.4 H; 544/55, 126, 96

[56] References Cited

U.S. PATENT DOCUMENTS

| 3,514,464 | 5/1970 | Pars et al. | 260/295 |
| 3,535,327 | 10/1970 | Pars et al. | 260/295 |
| 3,787,424 | 1/1974 | Pars et al. | 260/295 T |

*Primary Examiner*—Natalie Trousof
*Assistant Examiner*—Richard A. Schwartz
*Attorney, Agent, or Firm*—Robert L. Niblack; Gildo E. Fato

[57] ABSTRACT

Heterocyclic esters of alkylphenyl benzopyranopyridines represented by the formula

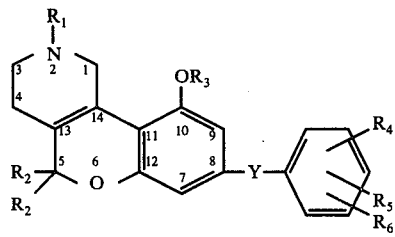

wherein $R_1$ is hydrogen, loweralkyl, loweralkanoyl, cycloalkylloweralkyl, cycloalkylloweralkanoyl, loweralkenyl, loweralkynyl, haloloweralkenyl, phenylloweralkyl, phenylloweralkenyl or phenylloweralkynyl; $R_2$ is loweralkyl; $R_3$ is

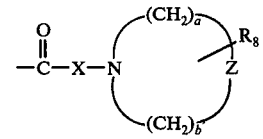

wherein X is a straight or branched chain alkylene group having from one to eight carbon atoms, a is an integer from 1 to 4, b is an integer from 1 to 4 and Z is $CH_2$, O, S or $NR_7$, with $R_7$ being hydrogen or loweralkyl, with the limitation that when X is O, S or $NR_7$, the sum of a and b is 3 or 4; and $R_8$ is hydrogen or loweralkyl; Y is a straight or branched chain alkylene group having from one to ten carbon atoms; and each $R_4$ and $R_5$ and $R_6$ are the same or different members of the group consisting of hydrogen, halo, trifluoromethyl or loweralkyl; and the pharmaceutically acceptable acid addition salts thereof.

7 Claims, No Drawings

HETEROCYCLIC ESTERS OF ALKYLPHENYL BENZOPYRANOPYRIDINES

DETAILED DESCRIPTION OF THE INVENTION

This invention relates to novel alkylphenyl benzopyranopyridines and to heterocyclic esters thereof, to methods of preparing the compounds, to pharmaceutical compositions containing the compounds and to use of the compounds and pharmaceutical compositions containing the compounds for pharmacological and medicinal purposes.

According to one aspect of this invention, compounds are provided which can be represented by the formula

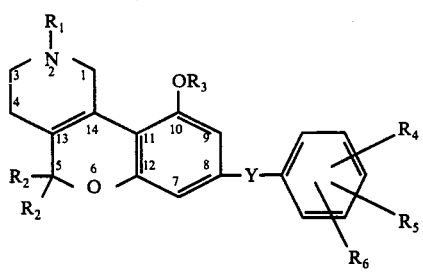

wherein $R_1$ is hydrogen, loweralkyl, loweralkanoyl, cycloalkylloweralkyl, cycloalkylloweralkanoyl, loweralkenyl, loweralkynyl, haloloweralkenyl, phenylloweralkyl, phenylloweralkenyl or phenylloweralkynyl; $R_2$ is loweralkyl; $R_3$ is

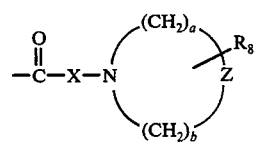

wherein X is a straight or branched chain alkylene group having from one to eight carbon atoms, $a$ is an integer from 1 to 4, $b$ is an integer from 1 to 4 and Z is $CH_2$, O, S or $NR_7$, with $R_7$ being hydrogen or loweralkyl, with the limitation that when X is O, S or $NR_7$, the sum of $a$ and $b$ is 3 or 4; and $R_8$ is hydrogen or loweralkyl; Y is a straight or branched chain alkylene group having from one to ten carbon atoms; and each $R_4$ and $R_5$ and $R_6$ are the same or different members of the group consisting of hydrogen, halo, trifluoromethyl or loweralkyl; and the pharmaceutically acceptable acid addition salts thereof.

The term "loweralkyl" as used herein, refers to $C_1$-$C_6$ straight or branched chain alkyl groups including methyl, ethyl, n-propyl, iso-propyl, n-butyl, sec-butyl, tert-butyl, n-pentyl, iso-pentyl, neo-pentyl, n-hexyl and the like.

The term "loweralkenyl" refers to straight and branched chain $C_2$-$C_6$ alkyl radicals from which a hydrogen atom has been removed from each of two adjacent carbon atoms to produce ethylenic unsaturation; e.g., vinyl, allyl, methallyl, 1-pentenyl and the like.

The term "loweralkynyl" refers to $C_2$-$C_6$ alkyl groups as defined above, from which two hydrogen atoms have been removed from each of two adjacent carbon atoms to produce acetylenic unsaturation; e.g., ethynyl, propargyl, 2-butynyl, 1-pentynyl and the like groups.

The term "halo" includes chloro, fluoro, bromo and iodo.

The term "loweralkanoyl" refers to saturated monovalent, aliphatic radicals derived from a monocarboxylic acid, including straight or branched chain radicals of from one to six carbon atoms including the formyl, acetyl, propionyl, α-methylpropionyl, butyryl, hexanoyl and the like radicals.

"Cycloalkyl," as used herein, refers to cyclic saturated aliphatic radicals having three to eight carbon atoms in a ring, such as cyclopropyl, cyclobutyl, cyclopentyl, cyclohexyl, cycloheptyl and cyclooctyl.

"Cycloalkylloweralkyl" refers to groups such as cyclopropyl-methyl, 2-methylcyclobutyl and the like.

The term "pharmaceutically acceptable acid addition salts" refers to non-toxic salts prepared by reacting the basic esters of the benzopyranopyridines with an organic or inorganic acid, or by reacting the benzopyranopyridines with the salt of an appropriate acid. Representative salts include the hydrochloride, hydrobromide, sulfate, bisulfate, acetate, valerate, oleate, laurate, borate, benzoate, lactate, phosphate, tosylate, citrate, maleate, succinate, tartrate, napsylate and the like.

Generally speaking, the starting materials, the corresponding phenols ($R_3$ = hydrogen) can be prepared by the following reaction schemes:

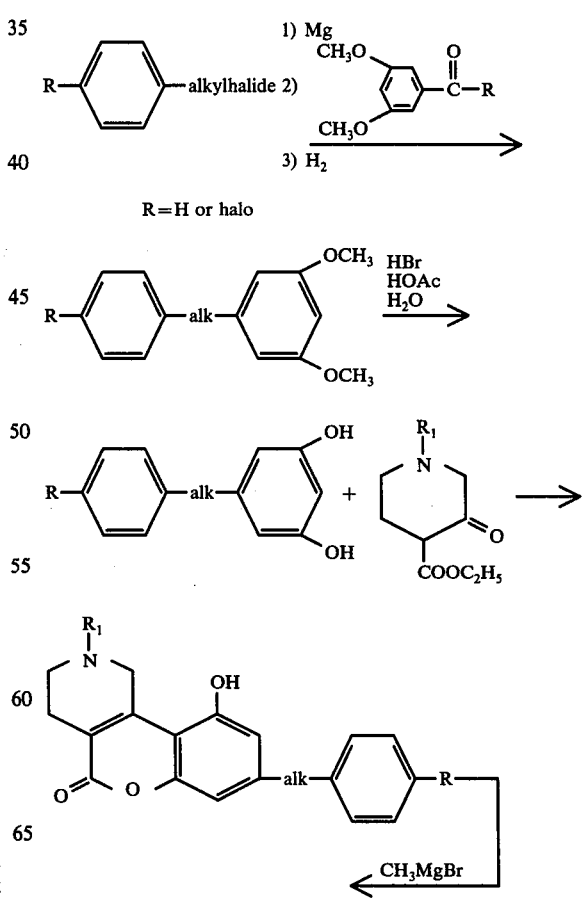

-continued
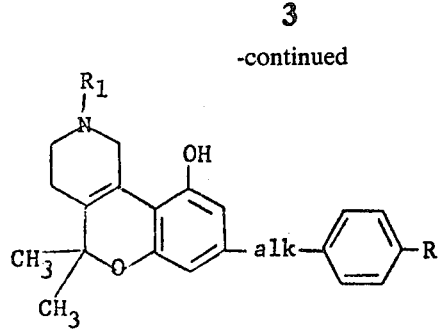
Alternative synthetic routes are represented by the following reaction schemes:
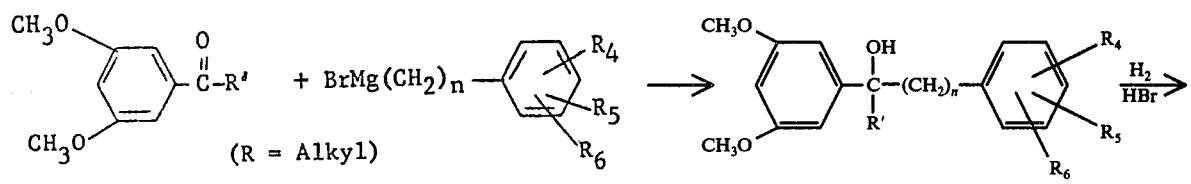
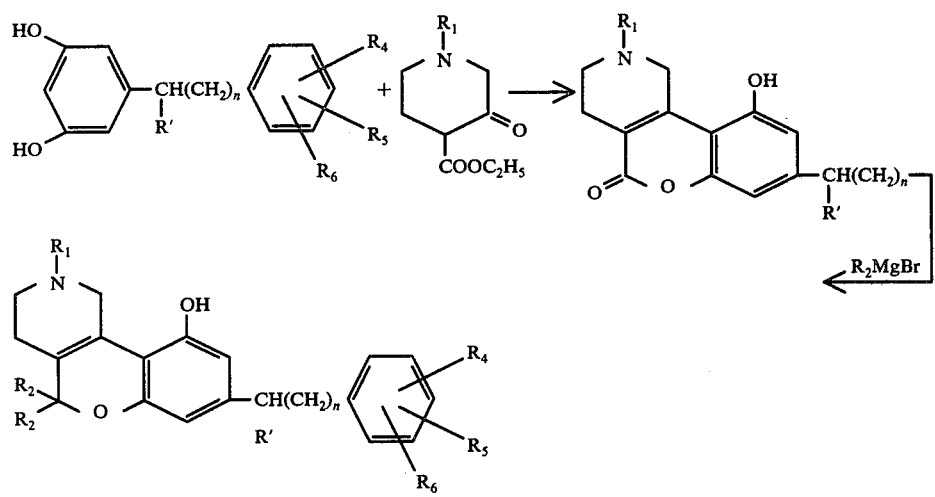
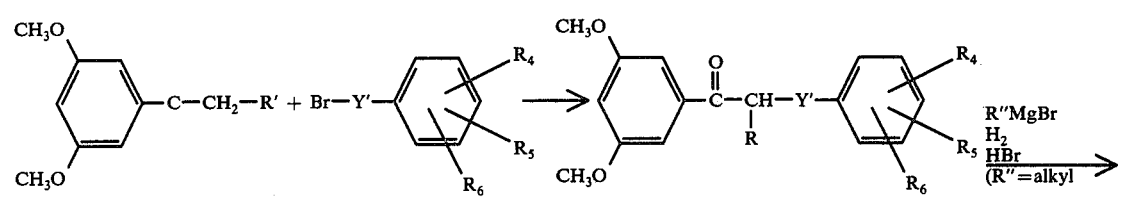
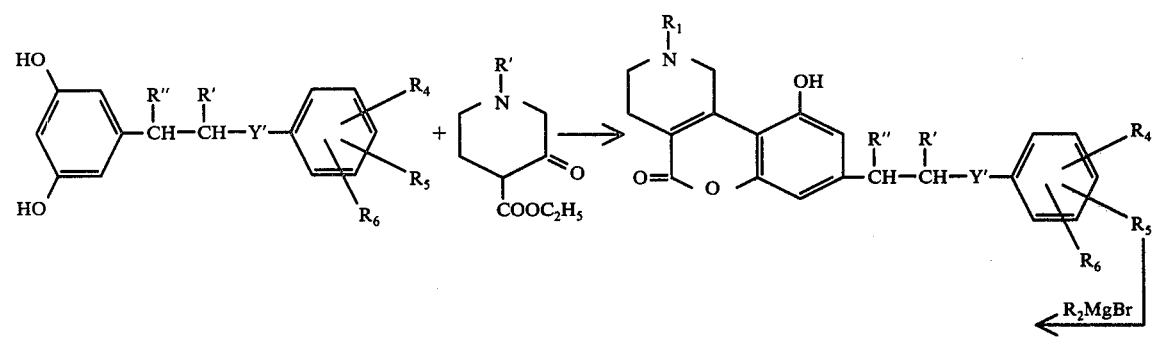
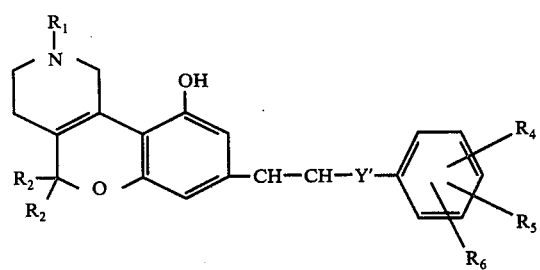

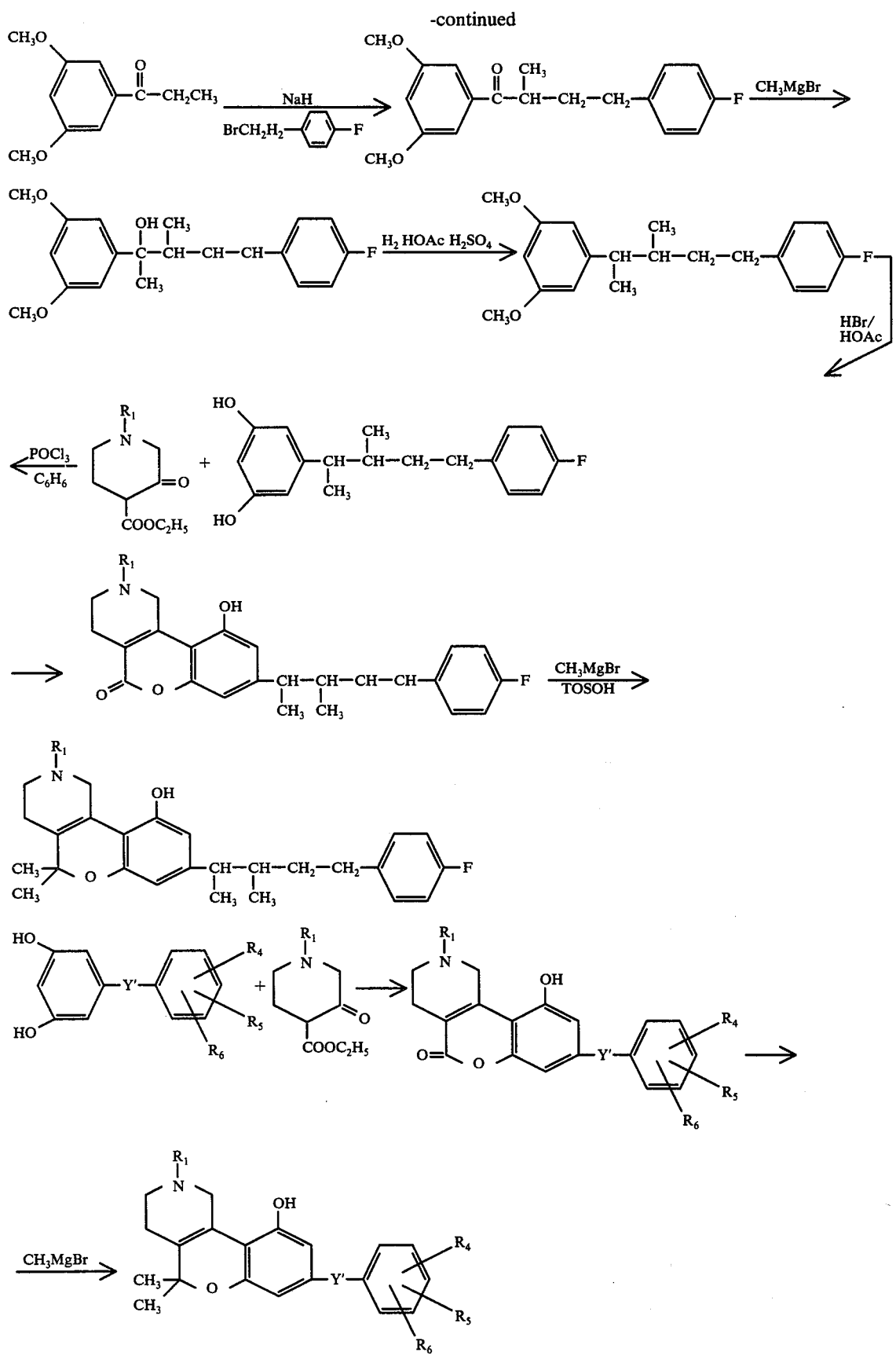
It is preferred that, in the preparation of the compounds of this invention, the pyrone of Formula III

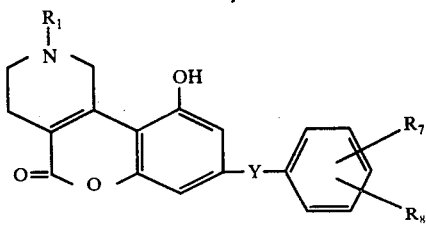

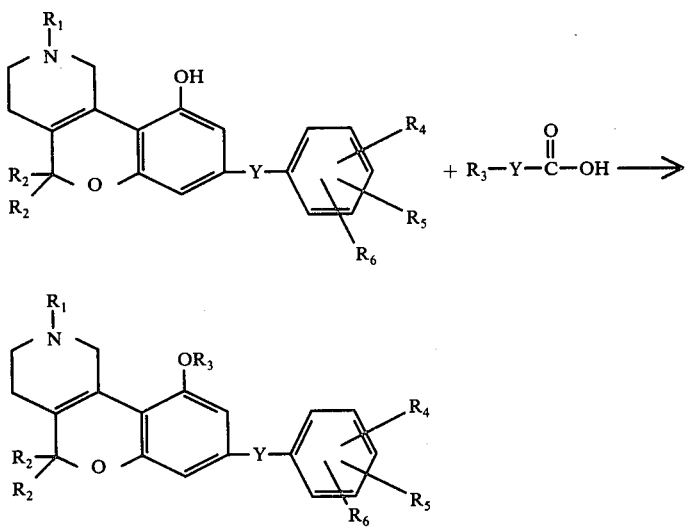

wherein $R_1$, $R_2$, $R_3$, $R_4$, $R_5$, $R_6$ and Y are defined above.

The benzopyranopyridine starting compounds and their preparation are disclosed in U.S. Pat. No. 3,576,798.

Some of the heterocyclic acids which can be used in the process of preparing the esters of this invention are:
γ-piperidinobutyric acid,
γ-morpholinobutyric acid,
γ-(2-methylpiperidino)-butyric acid,
δ-piperidinovaleric acid,
γ-pyrrolidinobutyric acid,
β-piperidinopropionic acid,
γ-thiomorpholinobutyric acid and homopiperidinoacetic acid Reaction between the benzopyranopyridine starting material and the heterocyclic acid, or salt thereof, is readily effected by combining about equimolar amounts of the reactants and a slight excess of carbodiimide such as dicyclohexylcarbodiimide. The reaction proceeds readily at room temperature and is generally completed in about 4 to 20 hours. After the reaction is terminated, the reaction mixture can be filtered to remove the by-product of dicyclohexylurea, and the solvent can be distilled off using a rotary evaporator. The residue can be directly crystallized from a suitable solvent such as benzene/ether or the residue can be chromatographed and the desired material isolated from the appropriate chromatographic fractions. If the basic esters are obtained, the acid addition salts such as those named above, if desired, can be prepared by methods well known in the art.

The compounds of this invention, in the form of the free bases, can be used as neutralizing agents since they form salts with acids.

The compounds of this invention can be formulated into various pharmaceutical dosage forms such as tablets, capsules, pills and the like, for immediate or susbe such that $R_1$ is benzyl. The N-benzyl intermediate is prepared by reacting the 1-benzyl-4-carbo-loweralkoxypiperidone of Formula IV with the appropriate alkylphenylresorcinol of Formula V. The reaction can be carried out in a mixture of concentrated sulfuric acid and phosphorus oxychloride or in the presence of other condensing agents, preferably methanesulfonic acid, and is illustrated by the equation:

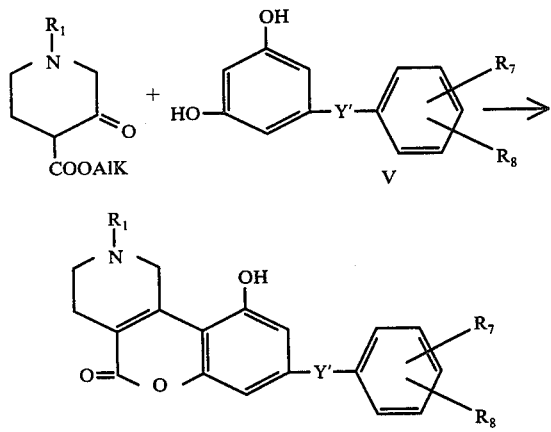

wherein $R_1$ is benzyl, Y' is as defined above and $R_7$ and $R_8$ are each hydrogen or loweralkyl.

N-benzyl-4-carbethoxy-3-piperidones of Formula IV can be prepared according to the procedure of Iselin, et al., Helv. Chim. Acta 37, 178–184 (1954) and McElvain et al., J. Am. Chem. Soc. 71, 896–900 (1948), or Phill and McElvain, J. Am. Chem. Soc. 55, 1233 (1933).

The 5-alkylphenyl or 5-haloalkylphenyl, etc. resorcinols of Formula V are conveniently prepared by methtained release, by combining the active compound with suitable pharmaceutically acceptable carriers or diluents according to methods well known in the art. Such dosage forms may additionally include excipients, binders, fillers, flavoring and sweetening agents and other therapeutically inert ingredients necessary in the formulation of the desired pharmaceutical preparation.

The following examples further illustrate this invention without, however, limiting it thereto.

The pharmacological activity of the compounds of this invention renders them useful as drugs although it should be understood that every compound of the invention will not necessarily have each activity possessed by the others.

The compounds of this invention are useful as analgesic agents, and generally at dosages of from 1 to 20 mg./kg. of body weight daily. In test animals, the compounds appear to be in the potency range of α-d-propoxyphene and codeine. The analgesic activity was first established in the rat tail flick method of Harris et al J.P.E.T., 169, 17 (1969) and the well-known acetic acid writhing and hot plate tests.

The compounds additionally exhibit anticonvulsant activity in test animals, and generally at dosages of from 10–40 mg./kg. of body weight.

EXAMPLE 1

Preparation of 2-(3,5-dimethoxyphenyl)-5-(4-fluorophenyl)pentane

A solution of 77 g. of 3-(4-fluorophenyl)propylbromide in 300 ml. of ether was added dropwise over a 2 hour period to a refluxing solution of 10 g of magnesium in 100 ml. of ether. The reaction mixture was refluxed for an additional 3 minutes after the addition was completed. A solution of 68 g. of 3,5-dimethoxyacetophenone in 100 ml. of ether was then added dropwise to the reaction and the reaction mixture was refluxed for 1½ hours. To the reaction was added 300 ml. of a saturated ammonium chloride solution dropwise with stirring. The layers were separated and the aqueous layer extracted with ether. The ether extract was dried over magnesium sulfate and the ether removed in vacuo to give an oil. An additional 111.7 g. of 3(4-fluorophenyl)-propylbromide was worked up in the above manner. The products from both runs were hydrogenated in ethanol-HCl using palladium as the catalyst. The solvents and catalyst were removed and the crude material distilled to yield 169.0 g. of 2-(3,5-dimethoxyphenyl)-5-(4-fluorophenyl)pentane, b.p. 145–155/0.05 mmHg.

Analysis Calcd. for $C_{19}H_{23}O_2F$: C, 75.60; H, 7.69 Found: C, 75.87; H, 7.98.

EXAMPLE 2

Preparation of 2-(3,5-dihydroxyphenyl)-5-(4-fluorophenyl)pentane

Fifty grams of the above prepared 2-(3,5-dimethoxyphenyl)-5-(4-fluorophenyl)pentane, 450 ml. of acetic acid and 180 ml. of 48% HBr in water were mixed. While cooling, the mixture was saturated with hydrogen bromide gas (approximately ½ hour). The reaction was placed in an 87° bath and stirred for 17 hours. The reaction was then concentrated in vacuo and the residue neutralized with $K_2CO_3$ and $NaHCO_3$, extracted with ether, treated with charcoal and $MgSO_4$ and filtered to yield 45 g. of 2-(3,5-dihydroxyphenyl)-5-(4-fluorophenyl)pentane as a brown oil which distills at 180°/0.01 mmHg.

Analysis Calcd. for $C_{17}H_{25}O_2F$: C, 74.20; H, 6.98; Found: C, 73.56; H, 7.04.

EXAMPLE 3

Preparation of 2-Benzyl-3-(4-fluorophenyl-1-methylbutyl)-10-hydroxy-5-oxo-1,2,3,4-tetrahydro-5H-[1]benzopyrano[3,4-d]pyridene hydrochloride To 45 g. of 2-(3,5-dihydroxyphenyl)-5-(4-fluorophenyl)pentane dissolved in 100 ml. of methanesulfonic acid were added in portions, 57 g. of 1-benzyl-3-keto-4-carbethoxy pyridene, hydrochloride. While stirring, 68 g. of $POCl_3$ were added and the solution was stirred for 5 days at room temperature. Water (300 ml.) and 180 ml. of $CHCl_3$ were then added and the reaction mixture stirred for 30 minutes. After the addition of 100 ml. of 15% NaOH, the reaction was stirred for an additional ten (10) minutes. The $CHCl_3$ layer was separated and extracted with 10% HCl. The $CHCl_3$ layer was concentrated and $CH_3CN$ added thereto to yield 55 g. of the desired product as the hydrochloride salt, m.p. 254°–256° C.

Theory: C, 70.80; H, 6.14; Cl, 6.97; N, 2.75; Found: C, 70.15; H, 6.17; Cl, 7.23; N, 2.74.

EXAMPLE 4

Preparation of 2-Benzyl-5,5-dimethyl-3-(4-fluorophenyl-1-methylbutyl)-10-hydroxy-1,2,3,4-tetrahydro-5H[1]benzopyrano[3,4-d]pyridene Sixty five grams of the above-prepared 2-Benzyl-3-(4-fluorophenyl-1-methylbutyl)-10-hydroxy-5-oxo-1,2,3,4-tetrahydro-5H-[1]benzopyrano[3,4-d]pyridene hydrochloride were suspended in 300 ml. of $CHCl_3$. After adding a $KHCO_3$ solution, the reaction was stirred for 30 minutes. The chloroform layer was separated, dried over $MgSO_4$, concentrated, taken up in benzene and concentrated again. The concentrate was taken up in 185 ml. of hot anisole and the resulting solution was added dropwise to a solution of $CH_3MgBr$ in anisole (prepared by adding 180 g. of $CH_3Br$ in 500 ml. of ether to 40 g. of Mg in 150 ml. of ether, evaporating the ether and adding 300 ml. of anisole). The reaction mixture was stored overnight at 62° C. Water (200 ml.) was added slowly, followed by 400 ml. of 10% $H_2SO_4$. The anisole was removed by steam distillation and the resulting solid was taken up in chloroform, neutralized with $KHCO_3$, dried over $MgSO_4$, concentrated and the product (36.5 g.), m.p. 188°–190° C., crystallized from $CH_3CN$.

EXAMPLE 5

Preparation of 5,5-Dimethyl-8-(4-fluorophenyl-1-methylbutyl)-10-hydroxy-2-[3-(1-propynyl)]-1,2,3,4-tetrahydro-5H[1]benzopyrano[3,4-d]pyridine hydrochloride 32.8 g. of the above-prepared 2-Benzyl-5,5-dimethyl-3-(4-fluorophenyl-1-methylbutyl)-10-hydroxy-1,2,3,4-tetrahydro-5H[1]benzopyrano[3,4-d]pyridene was hydrogenated in ethanol. The catalyst was removed, the solution concentrated, and the desired product was crystallized from ethanol-Skelly B as 19.9 g. of amorphous solid, m.p. 222°–225° C.

Theory: C, 69.50; H, 7.23; N, 3.24; Cl, 8.21; Found: C, 69.67; H, 7.34; N, 3.12; Cl, 8.10.

EXAMPLE 6

Preparation of
5,5-Dimethyl-8-(4-fluorophenyl-1-methylbutyl)-10-hydroxy-2-[3-(1-propynyl)]-1,2,3,4-tetrahydro-5H[1]benzopyrano[3,4-d]pyridine 5,5-Dimethyl-3-(4-fluorophenyl-1-methylbutyl)-10-hydroxy-1,2,3,4-tetrahydro-5H[1]benzopyrano[3,4-d]pyridine hydrochloride (19.9 g.) was dissolved in 88 ml. of dimethylformamide. While the solution was cooling, 3.14 g. of propargyl bromide were added. The reaction was stirred at room temperature for 15 hours. Water (120 ml.) was added slowly, whereupon the desired product crystallized. The crystalline product was washed with water and recrystallized from ether and $CH_3CN$ to yield 5.90 g. of the desired product, m.p. 164°–166° C.

Theory: C, 77.25; H, 7.46; N, 3.21; Found: C, 76.80; H, 7.76; N, 3.11.

EXAMPLE 7

Preparation of
5,5-Dimethyl-8-(4-fluorophenyl-1-methylbutyl)-10-[4-(piperidino)butyryloxy]-2-(2-propynyl)-1,2,3,4-tetrahydro-5H[1]benzopyrano[3,4-d]pyridine hydrochloride 5,5-Dimethyl-8-(4-fluorophenyl-1-methylbutyl)-10-hydroxy-2-[3-(1-propynyl)]-1,2,3,4-tetrahydro-5H[1]benzopyrano[3,4-d]pyridine (4.528 g.) was dissolved in 125 ml. of methylene chloride and combined with 2.246 g. of γ-piperidinobutyric acid hydrochloride and 2.357 g. of dicyclohexylcarbodiimide (Cruickshank and Sheehan, J. Am. Chem. Soc., 83, 2891 (1961), m.p. 190°–192° C.). The reaction mixture was stirred at room temperature for 16 hours. The insoluble byproduct of dicyclohexylurea was separated by filtration and the methylene chloride was removed using a rotary evaporator. The residue was crystallized from 15 ml. of methylene chloride and 30 ml. of ether to yield 6.4 g. of the desired product as a white solid, m.p. 108°–119° C. (decomp.).

Theory: C, 71.29; H, 7.71; N, 4.49; Cl, 5.68; Found: C, 69.88; H, 7.92; N, 4.30; Cl, 6.59.

NMR showed the presence of 1½% of methylene chloride in the product, which accounted for the analysis.

EXAMPLE 8

5,5-Dimethyl-10-[4-(morpholino)butyryloxy]-8-4-fluorophenyl-1-methylbutyl)-2-(2-propynyl)-1,2,3,4-tetrahydro-5H[1]benzopyrano[3,4-d]pyridine hydrochloride Equimolar amounts of 5,5-Dimethyl-10-hydroxy-8-(4-fluorophenyl-1-methylbutyl)-2-(2-propynyl)-1,2,3,4-tetrahydro-5H[1]benzopyrano[3,4-d]pyridine, γ-morpholinobutyric acid hydrochloride (Cruickshank and Sheehan, J.A.C.S. 83, 2891 (1961) and dicyclohexylcarbodiimide are combined in methylene chloride and stirred for 16 hours at room temperature. The insoluble by-product of dicyclohexylurea is removed by filtration and the methylene chloride is distilled off using a rotary evaporator. The residue is dissolved in a small amount of benzene and ether was added to give the crude product which can be recrystallized from methylene chloride/ligroin.

EXAMPLE 9

5,5-Dimethyl-10-[4-(2-methylpiperidino)butyryloxy]-8-(4-fluorophenyl-1-methylbutyl)-2-(2-propynyl)-1,2,3,4-tetrahydro-5H[1]benzopyrano[3,4-d]pyridine hydrochloride Methyl γ-(2-methylpiperidino) butyrate is dissolved in an 18% hydrochloric acid solution (90 ml. water and 90 ml. concentrated hydrochloric acid) and refluxed for 16 hours. The excess water is removed using reduced pressure (water aspirator) to give a semi-solid residue which is triturated with acetone and filtered to yield γ-(2-methylpiperidino) butyric acid hydrochloride as colorless crystals, m.p. 180°–182° C.

A mixture of equimolar quantities of 5,5-dimethyl-10-hydroxy-8-(4-fluorophenyl-1-methylbutyl)-2-(2-propynyl)-1,2,3,4-tetrahydro-5H[1]benzopyrano[3,4-d]pyridine, γ-(2-methylpiperidino)butyric acid hydrochloride and dicyclohexylcarbodiimide in methylene chloride are stirred at room temperature for 16 hours. The reaction mixture is cooled and the solid removed by suction filtration. The methylene chloride is evaporated to give a residue which is dissolved in methylene chloride and diethyl ether. After removing the resulting crude product, the solvents are evaporated and the gummy resin is dried, triturated with diethyl ether, and dried to yield the desired product.

EXAMPLE 10

5,5-Dimethyl-10-[5-(piperidino)valeryloxy]-8-(4-fluorophenyl-1-methylbutyl)-2-(2-propynyl)-1,2,3,4-tetrahydro-5H[1]benzopyrano[3,4-d]pyridine hydrochloride A mixture of 0.167 mole of methyl δ-chlorovalerate and 0.25 mole of sodium iodide in 120 ml. of acetone is stirred and heated at reflux for 16 hours. After cooling the mixture, a solid is removed by suction filtration, and the acetone is distilled off using a rotary evaporator. The residue is dissolved in 300 ml. of diethyl ether, and additional solid is removed by filtration. The ethereal solution is washed twice with a 10% sodium thiosulfate solution, once with water and dried over sodium sulfate. The ether is evaporated and the residue distilled at b.p. 107°–110° C. (15 mm.) to give 30.0 g. (74%) of methyl δ-iodovalerate as a light yellow liquid.

30.0 g. (0.124 mole) of methyl δ-iodovalerate and 42.5 g. (0.50 mole) of piperidine are dissolved in 250 ml. of benzene and heated at 60° C. for 3 hours with stirring. A colorless solid begins to appear shortly after the materials are combined. The solid is removed by suction filtration, and the benzene evaporated to give methyl δ-piperidinovalerate which distills as 23.5 g. (95%) of colorless liquid, b.p., 122°–24° C. (12.5 mm.).

23.5 g. (0.117 mole) of methyl δ-piperidinovalerate is dissolved in a combination of 125 ml. of concentrated hydrochloric acid and 125 ml. of water and refluxed with stirring for 16 hours. The excess water is removed using reduced pressure (water aspirator) to give a semi-solid residue which is triturated with acetone, filtered and dried. 21.0 g. (79%) of colorless crystals of δ-piperidinovaleric acid hydrochloride are obtained, m.p. of 202°–204° C.

A mixture of 2.4 g. (6.06 mm.) of 5,5-dimethyl-10-hydroxy-8-(4-fluorophenyl-1-methylbutyl)-2-(2-propynyl)-1,2,3,4-tetrahydro-5H[1]benzopyrano[3,4-d]pyridine, 1.35 g. (6.06 mm.) of δ-piperidinovaleric acid hydrochloride and 1.30 g. (6.30 mm.) of dicyclohexylcarbodiimide in 100 ml. of methylene chloride are stirred at room temperature for 5 hours. The reaction mixture is cooled overnight in the refrigerator and the by-product of dicyclohexylurea removed by suction filration. The mother liquor is evaporated and the residue dissolved in a mixture of methylene chloride/cyclohexane and allowed to stand in the cold for 2 hours. Gravity filtration separates the small amount of solid which appears, and the solvents are removed using a rotary evaporator. Crystallization from methylene chloride/diethyl ether yields the desired product.

EXAMPLE 11

5,5-Dimethyl-10-[4-(pyrrolidino)butyryloxy]-8-3(4-fluorophenyl-n-pentyl)-2-(2-propynyl)-1,2,3,4-tetrahydro-5H [1]benzopyrano[3,4-d]pyridine dihydrochloride 30.0 g. (0.13 mole) of methyl γ-iodobutyrate [Blicke et al, J. Am Chem. Soc., 63, 2488 (1941)] are combined with 36 g. (0.5 mole) of pyrrolidine in 300 ml. of benzene, heated at 60° C. for 0.5 hour and stirred at room temperature for 16 hours. A dark layer forms and the benzene solution is decanted, concentrated and distilled to give the crude product. This material is dissolved in a combination of 50 ml. of concentrated hydrochloric acid and 50 ml. of water and heated at reflux for 28 hours. The solution is concentrated under reduced pressure to give a semi-solid residue which is triturated with acetone and filtered. Recrystallization from a combination of 11 ml. of acetic acid/40 ml. of acetone yields 8.3 g. (33%) of colorless crystals of γ-pyrrolidinobutyric acid hydrochloride, m.p. 126°–127° C.

3.0 g. (7.57 mm.) of 5,5-dimethyl-10-hydroxy-8-(4-fluorophenyl-n-pentyl)-2-(2-propynyl)-1,2,3,4-tetrahydro-5H[1]benzopyran[3,4-d]pyridine is combined with 1.45 g. (7.57 mm.) of γ-pyrrolidinobutyric acid hydrochloride and 1.67 g. (8.12 mm.) of dicyclohexylcarbodiimide in 150 ml. of methylene chloride and stirred at room temperature for 3 hours. The reaction mixture is stored for 16 hours in the cold, and the by-product of dicyclohexylurea removed by suction filtration. After evaporation of the solvents, the resulting residue is dissolved and allowed to stand at room temperature for 2 hours and at 5° C. for 16 hours. A small quantity of solid is separated by gravity filtration, and the solvents are removed on a rotary evaporator. Crystallization from methylene chloride and diethyl ether give the desired product as the dihydrochloride.

EXAMPLE 12

5,5-Dimethyl-10-[4-(piperidino)butyryloxy]-2-(2-propynyl)-8-(1-methyl butylphenyl)-1,2,3,4-tetrahydro-5H[1]benzopyrano [3,4-d]pyridine hydrochloride A mixture of 1.45 g. (4.26 mm) of 5,5-dimethyl-10-hydroxy-2-(2-propynyl)-8-(1-methylbutylphenyl)-1,2,3,4-tetrahydro-5H[1]benzopyrano[3,4-d]pyridine, 0.89 g. (4.28 mm.) of γ-piperidinobutyric acid hydrochloride and 0.93 g. (4.50 mm.) of dicyclohexylcarbodiimide in 200 ml. of methylene chloride are stirred at room temperature for 18 hours. After cooling the reaction mixture for 1½ hours, the by-product of dicyclohexylurea is removed by suction filtration. A rotary evaporator is used to remove the methylene chloride, and a mixture of 25 ml. of methylene chloride and 50 ml. of cyclohexane is added. After standing at room temperature for 2 hours and a 5° C. for 16 hours, gravity filtration is used to separate the resulting solid. This material is generally a mixture of the starting acid hydrochloride and the hydrochloride salt of the starting benzopyran. The mother liquid is evaporated and the residue crystallized from a mixture of 2 ml. of methylene chloride and 15 ml. of diethyl ether. After filtration and drying, the pure product is obtained.

EXAMPLE 13

5,5-Dimethyl-8-(ethylphenyl)-10-[4-(piperidino)-butyryloxy]-2-(2-propynyl)-1,2,3,4-tetrahydro-5H[1]benzopyrano [3,4-d]pyridine hydrochloride Equimolar quantities of 5,5-dimethyl-10-hydroxy-8-(ethylphenyl)-2-(2-propynyl)-1,2,3,4-tetrahydro-5H[1]benzopyran, dicyclohexylcarbodiimide and γ-piperidinobutyric acid hydrochloride are combined in methylene chloride. After stirring for about 16 hours at room temperature, the reaction mixture was cooled, and the by-product of dicyclohexylurea is removed by suction filtration. The mother liquor is evaporated to give a residue which is dissolved in a methylene chloride/cyclohexane mixture and stored in the cold for 16 hours. A small quantity of additional dicyclohexylurea is removed by filtration, and the solvents are distilled off using a rotary evaporator. The residue which remained is dried in vacuo and crystallized from a mixture of methylene chloride and diethyl ether to give the desired product. A second crop of material can be obtained by workup of the mother liquor.

EXAMPLE 14

5,5-Dimethyl-10-[2-methyl-4-(piperidino)butyryloxy]-8-(4-fluorophenyl-1-methylbutyl)-2-(2-propynyl)-1,2,3,4-tetrahydro-5H[1]benzopyrano[3,4-d]pyridine hydrochloride The method of Lee V. Phillips (U.S. Pat. No. 3,299,100) is used to prepare α-methyl-γ-butyrolactone and this material is converted to ethyl γ-bromo-α-methylbutyrate via the procedure of G. Jones and J. Wood, "The Synthesis of 9-Azasteroids-II," Tetrahedron, 21, 2961 (1965).

10.5 g. (0.05 mole) of ethyl γ-bromo-α-methylbutyrate is combined with 17.0 g. (0.20 mole) of piperidine and 100 ml. of benzene, stirred for 16 hours at room temperature and heated at 60° C. for 4 hours. The reaction mixture is cooled and the colorless solid which appeared is removed by filtration. The mother liquor is concentrated to give ethyl α-methyl-γ-piperidinobutyrate as a mobile yellow liquid which distills (b.p. 78° at 0.25 mm.) as 6.7 g. (63%) of colorless liquid.

6.5 g. (0.030 mole) of ethyl α-methyl-γ-piperidinobutyrate are combined with a mixture of 45 ml. of water and 45 ml. of concentrated hydrochloric acid and heated at reflux for 16 hours. The solution is concentrated under reduced pressure (water aspirator) to give a residue which crystallizes upon addition of 50 ml. of diethyl ether. The ether is decanted, and the solid was triturated with acetone and filtered. Recrystallization from acetic acid/acetone gives 3.38 g. of α-methyl-γ-piperidinobutyric acid hydrochloride as colorless crystals, m.p. 166°–68°°C. and a second crop of 1.27 g. of solid, m.p. 165°–168° C. The total yield for both batches is 69%. The nuclear magnetic resonance and infrared spectra are in agreement with the proposed structure.

2.0 g. (5.05 mm.) of 5,5-dimethyl-10-hydroxy-8-(4-fluorophenyl-1-methylbutyl)-2-(2-propynyl)-1,2,3,4-tetrahydro-5H[1]benzopyrano[3,4-d]pyridine are combined with 1.12 g. (5.05 mm.) of α-methyl-γ-piperidino butyric acid hydrochloride and 1.08 g. (5.25 mm.) of dicyclohexylcarbodiimide in 110 ml. of methylene chloride and the mixture is stirred at room temperature for 16 hours. After cooling for 4 hours, the by-product of dicyclohexylurea is removed by suction filtration. The mother liquor is evaporated to give a colorless foamy residue which is dissolved in a methylene chloride/cyclohexane mixture and stored for 16 hours in the cold. A small amount of solid is separated by gravity filtration, and the solvents are removed using a rotary evaporator. The residue is dried to give a colorless solid which is dissolved in a mixture of methylene chloride/diethyl ether and converted to the dihydrochloride by the addition of a solution of hydrogen chloride in diethyl ether. The solvents are decanted, and the gummy residue crystallized upon trituration with diethyl ether. The solid is filtered and recrystallized from 20 ml. of methylene chloride/20 ml. diethyl ether to give the desired product.

EXAMPLE 15

5,5-Dimethyl-10-[4-(morpholino)butyryloxy]-8-(4-fluorophenyl-1-methylbutyl)-2-(2-propynyl)-1,2,3,4-tetrahydro-5H[1]benzopyrano[3,4-d]pyridine dihydrochloride 4.0 g. (10.1 mm.) of 5,5-dimethyl-10-hydroxy-8-(4-fluorophenyl-1-methylbutyl)-2-(2-propynyl)-1,2,3,4-tetrahydro-5H[1]benzopyrano[3,4-d]pyridine, 2.10 g. (10.1 mm.) of γ-morpholino-butyric acid hydrochloride and 2.18 g. (10.6 mm.) of dicyclohexylcarbodiimide are added to 200 ml. of methylene chloride. The reaction mixture is stirred at room temperature for 16 hours and after cooling, the by-product of dicyclohexylurea is removed by suction filtration. The mother liquor is evaporated to give a residue, which, after the usual workup, is converted to a dihydrochloride by the addition of an ether solution of hydrogen chloride. Recrystallization from methylene chloride/diethyl ether gives the final product.

EXAMPLE 16

5,5-Dimethyl-10-[3-(piperidino)propionyloxy]-8-(methylphenyl)-2-(2-propynyl)-1,2,3,4-tetrahydro-5H[1]benzopyrano-[3,4-d]pyridine tartrate 5,5-Dimethyl-10-hydroxy-8-(methylphenyl)-2-(2-propynyl)-1,2,3,4-tetrahydro-5H[1]benzopyrano[3,4-d]pyridine (1 mm.), dicyclohexylcarbodiimide (1 mm.) and β-piperidinopropionic acid (1 mm.) are combined in 30 ml. of methylene chloride and stirred for 16 hours. The insoluble by-product of dicyclohexylurea is removed by filtration and the methylene chloride is distilled off using a rotary evaporator. The residue is dissolved in benzene and filtered to remove any insoluble material. The solvent is evaporated and the residue is chromatographed to yield the desired product as neutral material which can be converted to the tartrate by well known methods.

The following compounds are prepared according to the method of Example 16 by reacting the desired benzopyranopyridine with the appropriate acid or acid salt.

EXAMPLE 17

5,5-Dimethyl-8-(4-fluorophenyl-1-methylbutyl)-2-(2-propynyl)-1,2,3,4-tetrahydro-10-[4-(thiomorpholino)-butyryloxy]-5H[1] benzopyrano[3,4-d]pyridine hydrobromide Equimolar amounts of 5,5dimethyl-10-hydroxy-8-(4-fluorophenyl-1-methylbutyl)-2-(2-propynyl)-1,2,3,4-tetrahydro-5H[1]benzopyrano[3,4-d]pyridine, γ-thiomorpholinobutyric acid hydrobromide and dicyclohexylcarbodiimide are reacted to form the desired product.

EXAMPLE 18

5,5-Dimethyl-2-benzyl-10-[2-(homopiperidino)acetoxy]-8-(4-fluorophenyl-n-hexyl)-1,2,3,4-tetrahydro-5H[1]benzopyrano[3,4-d]pyridine Equimolar amounts of 5,5-dimethyl-2-benzyl-8-(4-fluorophenyl-n-hexyl)-10-hydroxy-1,2,3,4-tetrahydro-5H[1] benzopyrano[3,4-d]pyridine, homopiperidinoacetic acid and dicyclohexylcarbodiimide are reacted to form the desired product.

EXAMPLE 19

5,5-Dimethyl-10-[4-morpholino)butyryloxy]-8-(3,4-difluorophenyl-n-pentyl)-2-methyl-1,2,3,4-tetrahydro-5H[1]benzopyrano[3,4-d]pyridine hydrochloride 5,5-Dimethyl-10-hydroxy-8-(3,4-difluorophenyl-n-pentyl)-1,2,3,4-tetrahydro-5H[1]benzopyrano[3,4-d]pyridine, γ-morpholino-butyric acid hydrochloride and dicyclohexylcarbodiimide are combined in equimolar amounts in methylene chloride and reacted as in Example 7 to give the desired product.

EXAMPLE 20

2-Benzyl-5,5-diethyl-10-[4-(morpholino)butyryloxy]-8-2,5-difluorophenyl-n-octyl-1,2,3,4-tetrahydro-5H[1]-benzopyrano[3,4-d]pyridine hydrochloride 2-Benzyl-5,5-dimethyl-10-hydroxy-8-(2,5-difluorophenyl-n-octyl)-1,2,3,4-tetrahydro-5H[1]benzopyrano[3,4-d] pyridine, γ-morpholino-butyric acid hydrochloride and dicyclohexylcarbodiimide are combined in equimolar amounts in methylene chloride and reacted as in Example 7 to give the desired product.

EXAMPLE 21

2-Benzyl-5,5-dimethyl-10-[4-(2-methylpiperidino)-butyryloxy]-8-(2-methyl-5-chlorophenyl-1-methylbutyl)-1,2,3,4-tetrahydro-5H[1]benzopyrano[3,4-d]pyridine hydrochloride 2-Benzyl-5,5-dimethyl-10-hydroxy-8-(2-methyl-5-chlorophenyl-1-methylbutyl)-1,2,3,4-tetrahydro-5H[1]benzopyrano[3,4-d]pyridine, γ-(2-methylpiperidino)-butyric acid hydrochloride and dicyclohexylcarbodiimide in equimolar amounts are reacted as in Example 7 to give the desired product.

EXAMPLE 22

5,5-Dimethyl-10-[4-(pyrrolidino)butyryloxy]-2-phenethyl-8-(4-chlorophenyl-1-methylbutyl)-1,2,3,4-tetrahydro-5H [1]benzopyrano[3,4-d]pyridine hydrochloride 5,5-Dimethyl-10-hydroxy-2-phenethyl-8-(4-chlorophenyl-1-methylbutyl)-1,2,3,4-tetrahydro-5H[1]3,4-d]pyridine, γ-pyrrolidino-butyric acid hydrochloride and dicyclohexylcarbodiimide are reacted in equimolar amounts according to Example 7 to produce the desired product.

EXAMPLE 23

2-Allyl-5,5-diethyl-8-(4-fluorophenyl-1-methylbutyl)-10-[4-(piperidino)butyryloxy]-1,2,3,4-tetrahydro-5H[1]benzopyrano[3,4-d]pyridine hydrochloride 2-Allyl-5,5-diethyl-8-(4-fluorophenyl-1-methylphenyl)-10-hydroxy-1,2,3,4-tetrahydro-5H[1]benzopyrano[3,4-d]pyridine, γ-piperidinobutyric acid hydrochloride and dicyclohexylcarbodiimide are reacted in equimolar amounts to produce the desired product.

EXAMPLE 24

2-(2-Cyclohexylethyl)-5,5-dimethyl-8-(4-fluorophenyl-1-methylphenyl)-10-[5-(morpholino)valeryloxy]-1,2,3,4-tetrahydro-5H[1]benzopyrano[3,4-d]pyridine hydrochloride 2-(2-Cyclohexylethyl)-5,5-dimethyl-10-hydroxy-8-(4-fluorophenyl-1-methylphenyl)-1,2,3,4-tetrahydro-5H[1]benzopyrano[3,4-d]pyridine, δ-piperidinovaleric acid hydrochloride and dicyclohexylcarbodiimide are reacted in equimolar amounts according to Example 7 to form the desired product.

EXAMPLE 25

2-Cinnamyl-8-(2,3-dimethylphenyl-n-heptyl)-5,5-di(n-propyl)-10-[4-(pyrrolidino)butyryloxy]-1,2,3,4-tetrahydro-5H[1]benzopyrano[3,4-d]pyridine hydrochloride 2-Cinnamyl-8-(2,3-dimethylphenyl-n-heptyl)-5,5-di(n-propyl)-10-hydroxy-1,2,3,4-tetrahydro-5H[1]benzopyrano [3,4-d]pyridine, γ-pyrrolidinobutyric acid hydrochloride and dicyclohexylcarbodiimide are reacted in equimolar amounts according to Example 1 to form the desired product.

The present invention includes within its scope, pharmaceutical compositions comprising, as an active ingredient, at least one of the compounds of this invention in association with a pharmaceutically acceptable carrier or diluent. The compounds of this invention exhibit both oral and parenteral activity and can be formulated in dosage forms for oral, parenteral or rectal administration.

Solid dosage forms for oral administration include capsules, tablets, pills, powders and granules. In such solid dosage forms, the active compound is admixed with at least one inert diluent such as sucrose, lactose or starch. Such dosage forms can also comprise, as is normal practice, additional substances other than inert diluents, e.g., lubricating agents such as magnesium stearate, and sweetening and flavoring agents. Tablets and pills can additionally be prepared with enteric coatings.

Liquid dosage forms for oral administration include pharmaceutically acceptable emulsions, solutions, suspensions, syrups and elixirs containing inert diluents commonly used in the art, such as water. Besides inert diluents, such compositions can also include adjuvants, such as wetting agents, emulsifying and suspending agents and sweetening, flavoring and perfuming agents.

Preparations according to this invention for parenteral administration include sterile aqueous or nonaqueous solutions, suspensions or emulsions. Examples of non-aqueous solvents or vehicles are propylene glycol, polyethylene glycol, vegetable oils, such as olive oil, and injectable organic esters such as ethyl oleate. Such dosage forms may also contain adjuvants such as preserving, wetting, emulsifying and dispersing agents. They may be sterilized by, for example, filtration through a bacteria-retaining filter, by incorporating sterilizing agents into the compositions, by irradiating the compositions, or by heating the compositions. They can also be manufactured in the form of sterile solid compositions which can be dissolved in sterile water, or some other sterile injectable medium immediately before use.

Compositions for rectal administration are suppositories which may contain in addition to the active substance, excipients such as cocoa butter or a suppository wax.

The dosage of active ingredient in the compositions of this invention may be varied; however, it is necessary that the amount of the active ingredient shall be such that a suitable dosage form is obtained. The selected dosage depends upon the desired therapeutic effect, on the route of administration and on the duration of the treatment. Generally, dosage levels of between 0.5 to 25 mg./kg. of body weight daily are administered to patients in need of analgesia or tranquilization.

The following example further illustrates the pharmaceutical compositions which are a feature of this invention:

EXAMPLE 26

Tablets weighing 200 mg. and having the following composition are prepared by standard tableting procedures:

| Ingredient | Mg. |
|---|---|
| 5,5-Dimethyl-8-(4-fluorophenyl-1-methylbutyl)-10-[4-(piperidino)butyryloxy]2-(2-propynyl)-1,2,3,4-tetrahydro-5H[1]benzopyrano[3,4-d] pyridine hydrochloride | 100 |
| Starch | 94 |
| Colloidal silica | 5 |
| Magnesium stearate | 1 |

It will be understood by those skilled in the art that the above composition can contain any of the compounds of this invention.

I claim:

1. A compound of the formula:

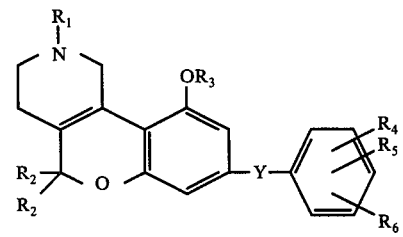

wherein $R_1$ is loweralkynyl; $R_2$ is methyl; $R_3$ is

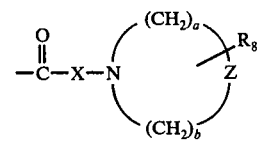

wherein X is a straight or branched chain alkylene group having from one to eight carbon atoms, a is an integer from 1 to 4, b is an integer from 1 to 4 and Z is $CH_2$, O, S or $NR_7$, with $R_7$ being hydrogen or loweralkyl, with the limitation that when Z is O, S or NR₇, the sum of a and b is 3 or 4; and R₈ is hydrogen or loweralkyl; Y is a straight or branched chain alkylene group having from one to ten carbon atoms; and each R₄ and R₅ and R₆ are the same or different members of the group consisting of hydrogen, halo, trifluoromethyl or loweralkyl; and the pharmaceutically acceptable acid addition salts thereof.

2. A compound in accordance with claim 1 wherein R₁ is propargyl.

3. A compound in accordance with claim 1 of the formula:

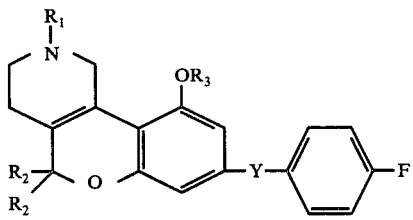

4. A compound in accordance with claim 3 wherein R₁ is loweralkynyl.

5. A compound in accordance with claim 4 wherein R₁ is propargyl.

6. A compound in accordance with claim 5 wherein each R₂ are methyl.

7. A compound in accordance with claim 6, 5,5-dimethyl-8-(4-fluorophenyl-1-methylbutyl)-10-[4-(piperidino)-butyryloxy]-2-(2-propynyl)-1,2,3,4-tetrahydro-5H[1]benzopyrano[3,4-d]pyridine hydrochloride.

* * * * *